United States Patent
Grehan et al.

(10) Patent No.: US 10,449,307 B2
(45) Date of Patent: *Oct. 22, 2019

(54) NEBULIZER VIBRATING APERTURE PLATE DRIVE FREQUENCY CONTROL AND MONITORING

(71) Applicant: Stamford Devices Limited, Galway (IE)

(72) Inventors: Joseph Grehan, Galway (IE); Niall Smith, Central Scotland (GB)

(73) Assignee: STAMFORD DEVICES LIMITED, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/933,082

(22) Filed: Mar. 22, 2018

(65) Prior Publication Data

US 2018/0214643 A1 Aug. 2, 2018

Related U.S. Application Data (63) Continuation of application No. 14/423,046, filed as application No. PCT/EP2014/060723 on May 23, 2014, now Pat. No. 9,956,356.

(30) Foreign Application Priority Data

Jul. 24, 2013 (EP) .................................... 13177909

(51) Int. Cl.
*A61M 11/00* (2006.01)
*B05B 17/06* (2006.01)
(Continued)

(52) U.S. Cl.
CPC ......... *A61M 11/005* (2013.01); *A61M 11/001* (2014.02); *B05B 15/14* (2018.02);
(Continued)

(58) Field of Classification Search
CPC .. A61M 11/00; A61M 11/001; A61M 11/005; A61M 2205/33;
(Continued)

(56) References Cited

U.S. PATENT DOCUMENTS 6,546,927 B2 4/2003 Litherland et al.
9,956,356 B2 * 5/2018 Grehan ................... B05B 15/14
(Continued)

FOREIGN PATENT DOCUMENTS

EP 1 558 315 B1 10/2005
EP 2 047 914 A1 4/2009
(Continued)

OTHER PUBLICATIONS

International Search Report and Written Opinion for International Application No. PCT/EP2014/060723, dated Aug. 26, 2014 (8 pages).

*Primary Examiner* — Lisa M Caputo
*Assistant Examiner* — Rose M Miller
(74) *Attorney, Agent, or Firm* — Bookoff McAndrews, PLLC (57) ABSTRACT

A nebulizer has an aperture plate, a mounting, an actuator, and an aperture plate drive circuit (2-4). A controller measures an electrical drive parameter at each of a plurality of measuring points, each measuring point having a drive frequency; and based on the values of the parameter at the measuring points makes a determination of optimum drive frequency and also an end-of-dose prediction. The controller performs a short scan at regular sub-second intervals at which drive current is measured at two measuring points with different drive frequencies. According to drive parameter measurements at these points the controller determines if a full scan sweeping across a larger number of measuring points should be performed. The full scan provides the (Continued)

optimum drive frequency for the device and also an end of dose indication.

20 Claims, 5 Drawing Sheets (51) Int. Cl.
| | |
|---|---|
| G01N 29/22 | (2006.01) |
| G01N 29/42 | (2006.01) |
| G06F 19/00 | (2018.01) |
| B05B 17/00 | (2006.01) |
| B06B 1/02 | (2006.01) |
| G16H 20/13 | (2018.01) |
| B05B 15/14 | (2018.01) |
| B05B 12/00 | (2018.01) |
| B05B 12/08 | (2006.01) |

(52) U.S. Cl.
CPC ...... *B05B 17/0646* (2013.01); *B05B 17/0669* (2013.01); *B06B 1/0253* (2013.01); *G01N 29/22* (2013.01); *G01N 29/42* (2013.01); *G06F 19/3456* (2013.01); *G16H 20/13* (2018.01); *A61M 2205/33* (2013.01); *A61M 2205/3317* (2013.01); *B05B 12/004* (2013.01); *B05B 12/081* (2013.01)

(58) Field of Classification Search
CPC ........ A61M 2205/3317; A61M 15/085; B05B 17/0646; B05B 17/0669; B05B 12/004; B05B 12/081; B06B 1/0253; G01N 29/22; G01N 29/42; G06F 19/3456
USPC ........... 128/200.11, 200.16; 73/658; 239/338
See application file for complete search history.

(56) References Cited

U.S. PATENT DOCUMENTS

| | | |
|---|---|---|
| 2003/0150446 A1 | 8/2003 | Patel et al. |
| 2005/0217666 A1 | 10/2005 | Fink et al. |
| 2006/0102172 A1 | 5/2006 | Feiner et al. |
| 2007/0240712 A1 | 10/2007 | Fleming et al. |
| 2012/0111970 A1 | 5/2012 | Hogan et al. |

FOREIGN PATENT DOCUMENTS

| | | |
|---|---|---|
| WO | WO 93/09881 | 5/1993 |
| WO | WO 2004/039442 A1 | 5/2004 |
| WO | WO 2009/118717 A1 | 10/2009 |
| WO | WO 2010/035251 A2 | 4/2010 |
| WO | WO 2010/035252 A2 | 4/2010 |
| WO | WO 2010/035252 A3 | 4/2010 |
| WO | WO 2011/091002 A1 | 7/2011 |

\* cited by examiner

NEBULIZER VIBRATING APERTURE PLATE DRIVE FREQUENCY CONTROL AND MONITORING

CROSS-REFERENCE TO RELATED APPLICATIONS

This application is a continuation application under 37 CFR § 1.53(b) of U.S. patent application Ser. No. 14/423,046, filed Feb. 20, 2015, which is a National Stage of PCT/EP2014/060723, filed May 23, 2014, which claims priority to European Patent Application No. EP13177909.2, filed Jul. 24, 2013. The contents of each of these are incorporated herein by reference in their entirety.

FIELD OF THE INVENTION

The invention relates to aerosol generators or nebulizers, having vibrating aperture plates to aerosolize medicaments.

PRIOR ART DISCUSSION

Examples of nebulizers are described in U.S. Pat. No. 6,546,927 (Litherland) and EP1558315 (PARI). These disclosures include techniques to predict the end of a liquid medicament dose on the aperture plate. These techniques are based on monitoring a parameter such as drive current at different drive frequencies.

The approach taught in the Litherland document involves detecting the present desired frequency, and the desired frequency may for example be the resonant frequency. Frequency is the variable that is swept, and a parameter is tracked. The tracking provides an indication of the desired drive frequency. This may change as the dose decreases in volume. For example, the resonant frequency may drift from 135 kHz to 140 kHz from a loaded state to an unloaded state. In Litherland the device can reduce power supplied to the aperture plate and/or provide a user indication as the dose is ending.

The present invention is directed towards providing improved frequency control. Specifically, it is desired to improve any one or all of faster frequency control response to changes in conditions, less impact on the nebulisation process, and improved ability to accurately predict end-of-dose when used with patients who inhale medication at different rates.

SUMMARY OF THE INVENTION

According to the invention, there is provided a nebulizer comprising a vibrating aperture plate, a mounting, an actuator, and an aperture plate drive circuit having a controller, wherein the controller is configured to:

- measure an electrical drive parameter at each of a plurality of measuring points each measuring point having a drive frequency; and
- based on the values of the parameter at the measuring points make a determination of optimum drive frequency and also an end-of-dose prediction,
- characterized in that,
- the controller is configured to perform a short scan at which a parameter is measured at each of two or more measuring points with different drive frequencies, and according to drive parameter measurements at these points determine if a full scan sweeping across a larger number of measuring points should be performed.

In one embodiment, the short scan has fewer than five, and preferably two measuring points (CPt #1. CPt #2).

In one embodiment, the controller is configured to compare measurements with tolerance ranges, and if a measurement falls outside its associated range a full scan is initiated. In one embodiment, the tolerance ranges are pre-defined.

In one embodiment, the short scan is performed at regular intervals. Preferably, the intervals are sub-second.

In one embodiment, the full scan has in the range of 5 to 300 measuring points. In one embodiment, the full scan has in the range of 100 to 300 measuring points.

In one embodiment, the controller is configured to dynamically determine from the full scan a frequency for at least one of the short scan measuring points.

In one embodiment, in the controller is configured to select a frequency value corresponding to lowest drive current as a frequency for a short scan measuring point. Preferably, said lowest drive current is determined to correspond to a resonant frequency, and a frequency value for the full scan measuring point with lowest drive current is stored for use as a short scan measuring point frequency.

In one embodiment, the parameter is aperture plate drive current.

In one embodiment, the controller is configured to, during a full scan:

- dynamically perform a plurality of iterations, and
- in each iteration compare the measured parameter against a measurement at a previous measuring point to determine end of dose and/or optimum drive frequency.

In one embodiment, a slope in parameter measurements is analysed to determine said indication in each iteration. In one embodiment, a slope value above a threshold indicates end of dose.

In another aspect, the invention provides a method of operation of a nebulizer comprising a vibrating aperture plate, a mounting, an actuator, and an aperture plate drive circuit having a controller, wherein the method comprise the steps of the controller:

- measuring an electrical drive parameter at each of a plurality of measuring points each measuring point having a drive frequency; and
- based on the values of the parameter at the measuring points make a determination of optimum drive frequency and also an end-of-dose prediction,
- wherein the controller performs a short scan at which a parameter is measured at each of two or more measuring points with different drive frequencies, and according to drive parameter measurements at these points determine if a full scan sweeping across a larger number of measuring points should be performed.

In one embodiment, the short scan has fewer than five, and preferably two measuring points (CPt #1. CPt #2).

In one embodiment, the controller compares measurements with tolerance ranges, and if a measurement falls outside its associated range a full scan is initiated.

In one embodiment, the short scan is performed at regular intervals, preferably sub-second. Preferably, the full scan has in the range of 5 to 300 measuring points, preferably 100 to 300 measuring points.

In one embodiment, the controller dynamically determines from the full scan a frequency for at least one of the short scan measuring points, and selects a frequency value corresponding to lowest drive current as a frequency for a short scan measuring point.

In one embodiment, said lowest drive current is determined to correspond to a resonant frequency, and a frequency value for the full scan measuring point with lowest drive current is stored for use as a short scan measuring point frequency.

In one embodiment, the parameter is aperture plate drive current.

In one embodiment, the controller during a full scan:

dynamically performs a plurality of iterations, and in each iteration compares the measured parameter against a measurement at a previous measuring point to determine end of dose and/or optimum drive frequency.

In one embodiment, a slope in parameter measurements is analysed to determine said indication in each iteration Preferably, a slope value above a threshold indicates end of dose.

DETAILED DESCRIPTION OF THE INVENTION

Brief Description of the Drawings

The invention will be more clearly understood from the following description of some embodiments thereof, given by way of example only with reference to the accompanying drawings in which.

FIG. 2 is a flow diagram for operation of the controller to determine when a full end-of-dose scan should be performed;

FIG. 3 is a flow diagram showing the full end-of-dose scan;

FIGS. 4 to 6 are plots showing aspects of change of drive current with frequency; and FIG. 7 is a plot showing variation of both flow rate and current with drive frequency.

Referring to FIG. 1 a drive circuit 1 for a nebulizer comprises an output drive stage 2 which provides the power required for transfer to the nebulizer load 5. A filtering stage 3 removes undesirable electrical noise from the drive signal, ensuring compliance with EMC requirements.

A high voltage resonant circuit (stage 4) conditions the drive signal to ensure efficient coupling of power to the nebulizer load 5.

The mechanical arrangement of aperture plate, actuator and mounting may be of the type which is known for example from our prior specification numbers WO2010035252 and US2012111970.

The circuit of FIG. 1 dynamically monitors drive current in order to determine in real time the resonant frequencies (where resonant frequencies refer to points of resonance and anti-resonance) to be used in the determination of the optimum operating frequency of the nebulizer, and to also determine end-of-dose in an integrated fashion.

Short Scan

Referring to FIG. 2 the controller performs a short scan multiple times each second. This involves measuring drive current at the normal drive frequency (CheckPoint #1, "CPt #1"), and measuring value of the drive current to the aperture plate. The current tolerance is predefined. The current typically only changes when a change of state of the aperture plate from wet to dry occurs Once a change is identified, it prompts a full scan.

If CPt #1 drive current is outside the current tolerance a flag is set for a full scan. If not, the frequency is changed to a second reference frequency. The latter is determined according to a full scan. The drive current value for the CPt #2 frequency is determined. Likewise, if it is outside the tolerance the full scan flag is set. This loop is repeated at regular intervals, multiple times per second.

The short scan is run at intervals in the order of every second or less. It only moves away from the normal operating frequency for less than 1/1000th of a second while it measures the current at this second point of measurement (CPt #2). This ensures that there is no discernible interruption of the nebulization process.

In summary, the purpose of the short scan is to determine if a full scan should be performed. If the drive current is outside of tolerance then the full scan is activated in order to determine the optimum operating frequency and also to detect end of dose. The short scan does not interfere with operation of the nebulizer because it measures at only two frequencies. One of these is the resonant frequency. CPt #2 is a resonant frequency. In this embodiment the output drive stage 2 drives at CPt #1 with a frequency of 128 KHz, which has been found to provide a good performance across a range of liquid viscosities.

In other embodiments it is possible that once the optimum drive frequency is determined it will be used for CPt #1.

Full Scan

Referring to FIG. 3 the flow to implement a full scan is illustrated. The frequency is incremented in steps between 140 kHz and 160 kHz. The step size will change depending on the resolution required. For example, in one application only one type of nebulizer may be used, therefore a simple scan using only 10 steps may be sufficient. However in an application using multiple types of nebulizer, a much larger number of steps will be required to give higher resolution, in order to distinguish between wet and dry of the different devices.

At each point in the full scan the aperture plate drive current is determined. This provides a plot of drive current vs. frequency as shown in FIG. 4. A section with a steep slope is shown in a box in FIG. 4 and in more detail in FIGS. 5 and 6. In each iteration the current maximum differential (i.e. slope) is registered. Hence, in the first phase of FIG. 3 the maximum differential is recorded in real time during the full scan.

The next phase of the logic of FIG. 3 is to dynamically record the minimum drive current value (point of anti-resonance). At the end of each loop if the drive current is lower than that recorded for the short scan CPt #2 the value is recorded, as is the corresponding frequency. The current value is recorded as the short scan CPt #2 drive current value.

As illustrated by the final steps the slope recorded in the first phase of this scan provides an indication of end of dose.

Importantly, this scan can be used to determine the optimum drive frequency, as described above. Importantly, real time determination of the resonant frequencies gives configurable options for changing operation of the nebulizer to the optimum drive frequency. The resonant frequency may be used for either of the short scan measuring points.

This visual interruption in the plume due to the full scan lasts for only 0.3 of a second. This has negligible effect on operation of the device.

The energy requirement of the aperture plate is directly proportional to the impedance offered by the plate during aerosolization. The impedance of the plate is measured by monitoring one or more electrical characteristics such as voltage, current, or phase difference, and in the above embodiment, drive current.

The impedance of the plate to aerosolization is monitored at the initial drive frequency (CPt #1) and the energy requirements can be determined to be within required limits for correct operation of the vibrating mesh nebulizer, at which point the drive may continue to operate at this frequency.

Alternatively, the frequency of operation of the drive circuit can be adjusted to determine the optimum operating point for the piezo-element. This can be the anti-resonance point (CPt #2 frequency), where the minimum energy consumption occurs (or an offset of this).

A higher frequency, beyond the point of anti-resonance, exists where the energy consumption maximizes and this point is termed the point of resonance.

These points can be used in determination of the optimum operating frequency for the creation of desired flow of aerosolized liquid. There are mechanical reasons why it is preferable not to drive at the resonant point, for example it may not result in the desired flow rate of the nebulizer or the desired particle size or may result in excessive mechanical stress on the aperture plate Referring to FIG. 7, the optimum drive frequency can be determined utilizing details of the electrical parameters captured by the full scan method. The determination of the point of anti-resonance (where current is minimized) and the point of resonance (where the current is maximized) can be used in choosing the optimum drive frequency.

Figure 7:
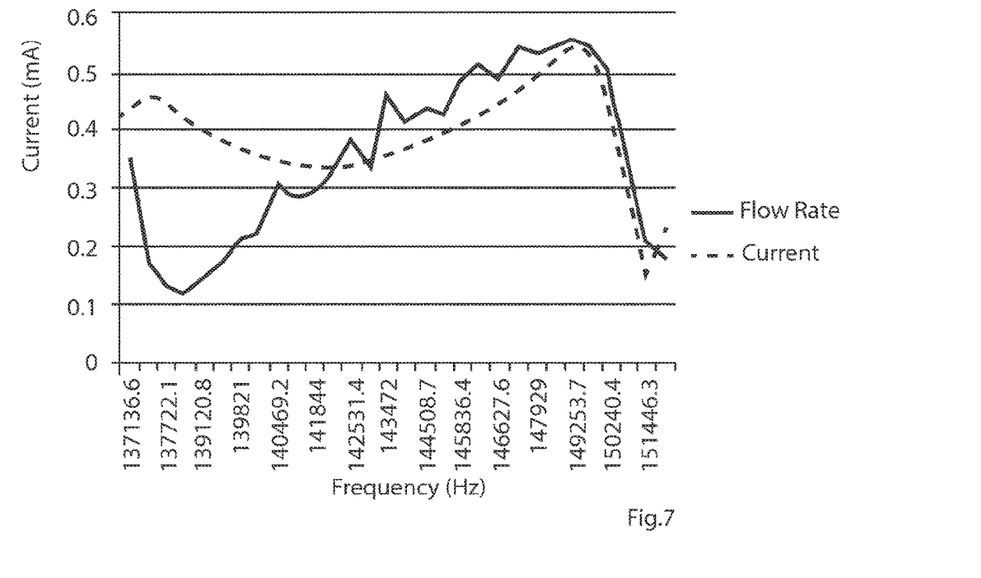

The point of resonance may provide the maximum flow rate, however this frequency may result in undesirable stresses on the mechanical structure. Runtime variation in the resonance point may also result in undesirable fluctuations in flow rate at this resonance point. Equally, the use of the anti-resonance point may not be desirable as the flow rate may not be sufficient at this point. The optimum frequency may be between these two points and the final frequency can be a fixed offset of one or more of these two points.

In FIG. 7 is might typically be the case that the operating frequency is chosen from the linear part between about 141 kHz and 150 kHz.

It will be appreciated that the state of aerosolization (wet/dry) can be determined by monitoring the rate of change of plate impedance between the anti-resonance and the resonance points (or an offset thereof). This is implemented by determining the maximum positive rate of change of impedance between the two resonant frequencies. A steep or abrupt rate of change indicates that no liquid is on the plate (DRY). A flat/gentle rate of change indicates the presence of liquid (WET).

Alternatively, a sudden change in the impedance of the plate at the initial frequency and/or the resonant (CPt #2) frequency can used as a quick method to indicate a possible change in aerosolization state (in the short scan). This is what triggers the full scan to actually determine the end of dose.

It will also be appreciated that the short scan provides much useful information for real time control, but does not cause a visible interruption in aerosolization. The short scan is run in advance of a full scan, which can cause a visible interruption in the aerosolization of liquid.

Figure 1:
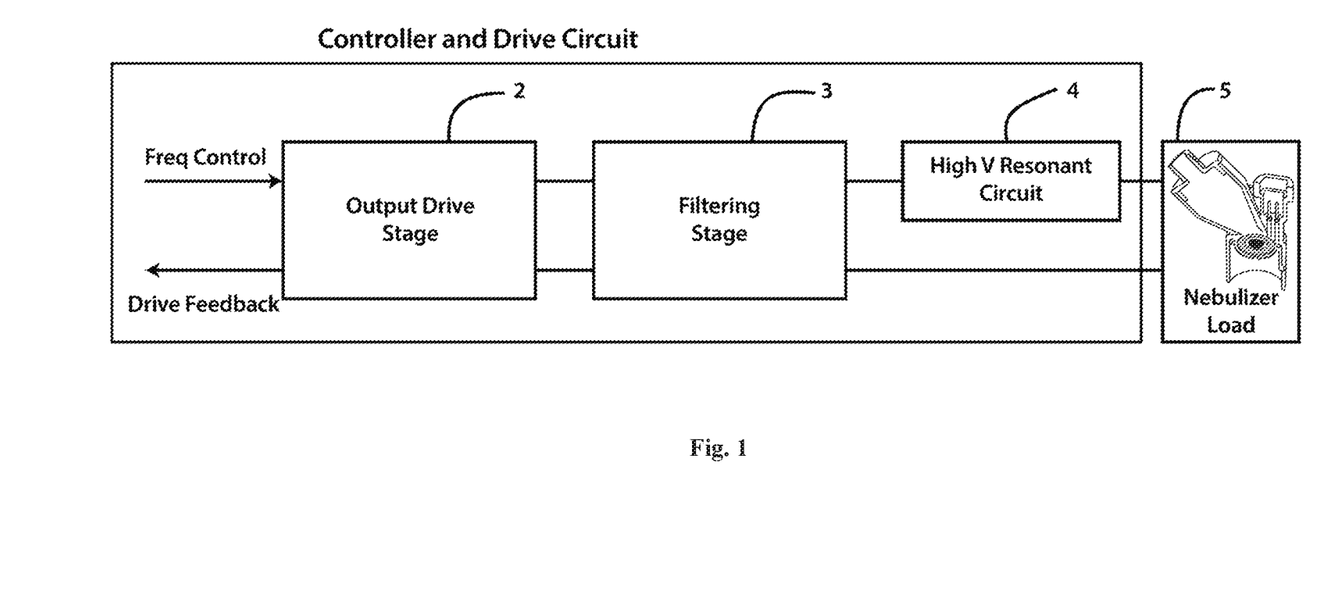
FIG. 1 is a diagram of a nebulizer drive circuit of the invention.
Figure 2:
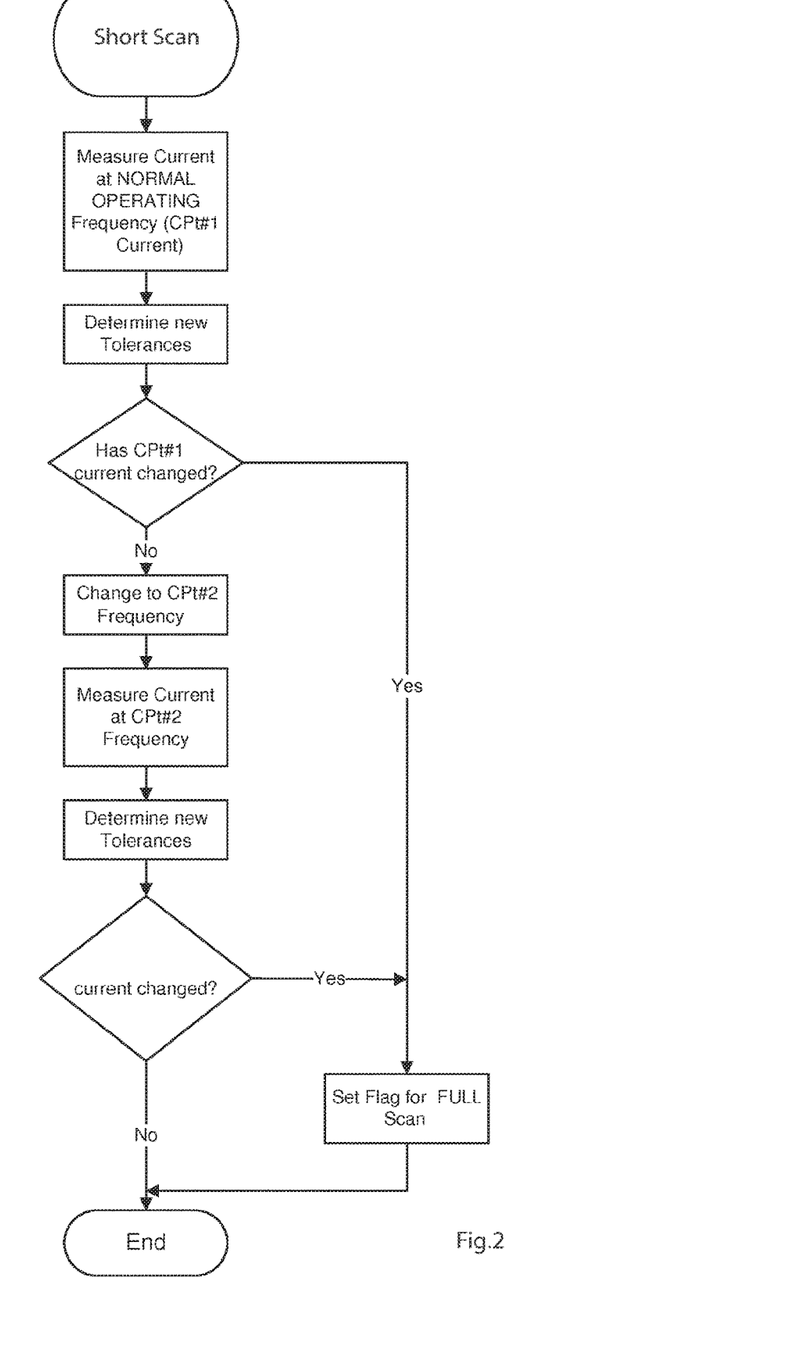
Figure 3:
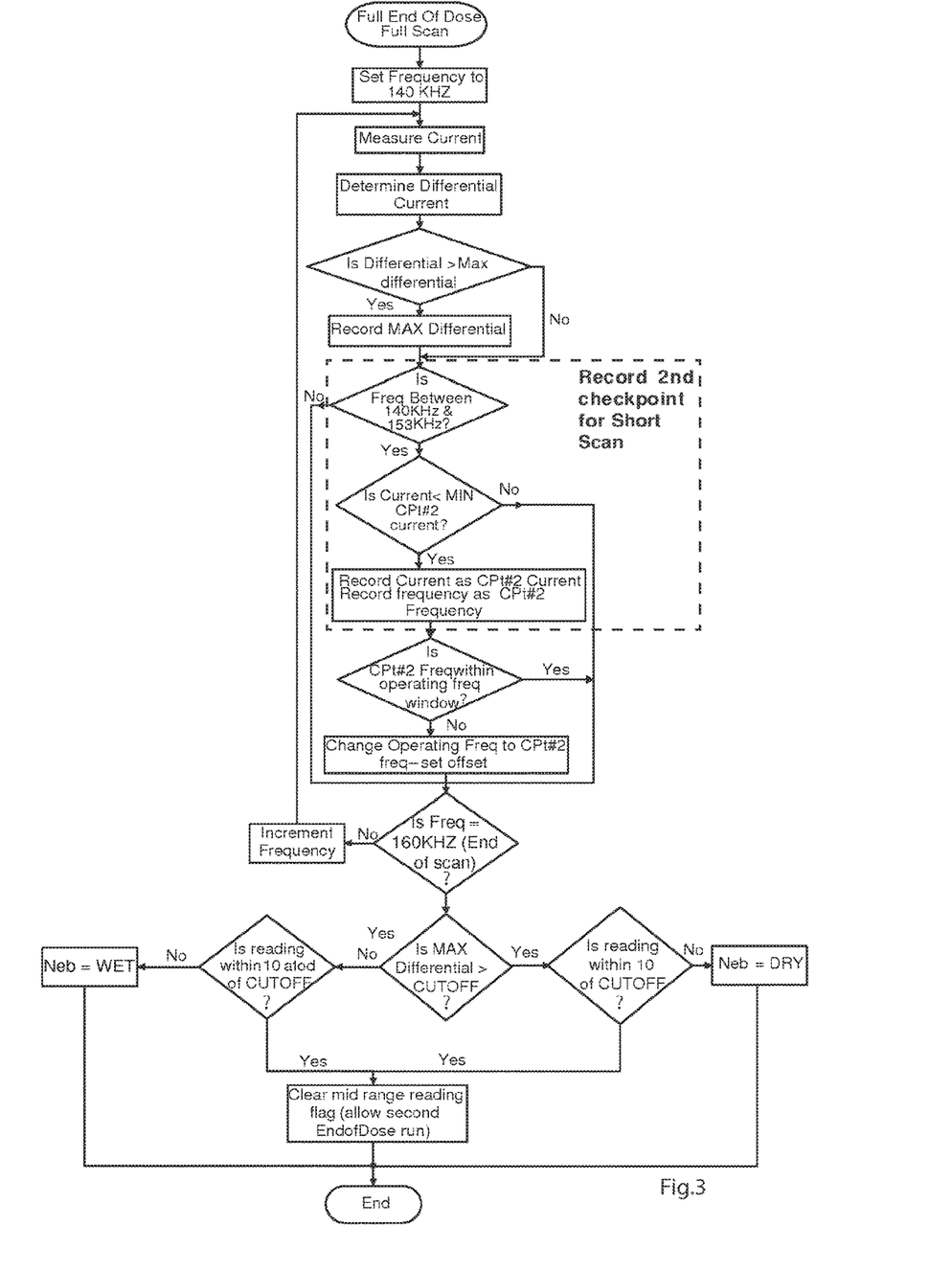
Figure 4:
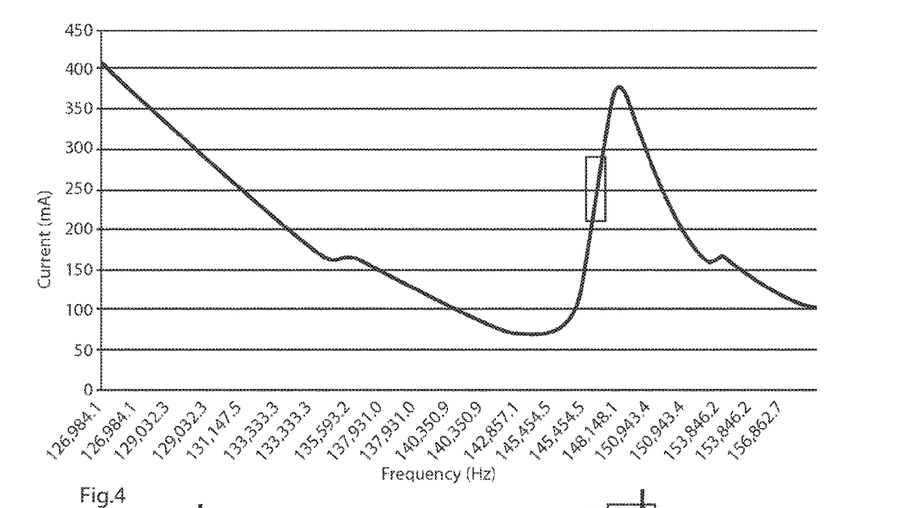
Figure 5:
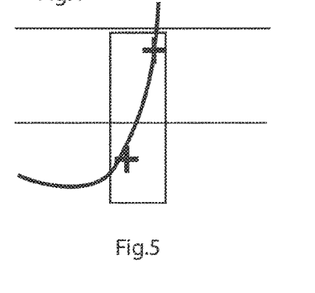
Figure 6:
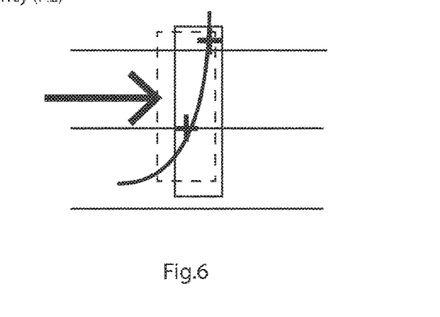

In summary, the software procedure implemented by the controller for determining the status of the nebulizer is as follows:
   Multiple times each second, the software will run a short scan (FIG. 2) to determine if a change of drive current has occurred.
   This change in drive current can indicate that the anti-resonance frequency and/or a change of state has occurred; therefore a full scan (FIG. 3) is requested.
   Upon completion of the full scan the status of the nebulizer is updated. (Wet or Dry).

In some embodiments, the controller may initiate a full scan after a predetermined time (such as a further 5 seconds). The purpose of this additional scan is to record the maximum slope after the device has completed 5 seconds in the new state. When a device changes state, the change in the current/slope profile is almost instantaneous. However, after an additional few seconds the new profile will have changed again slightly, due to changes in the mechanical structure of the plate, to a value that the nebulizer will maintain over a longer period of time. It is important to determine this stable value to ensure that the short scan has details of the correct frequency to monitor. When prompted by the short scan (or at predefined periods e.g. 5 seconds) the purpose of the predefined full scan may be to update the check points for the quick scan, as these two points may drift slightly during normal run mode.

The short scan checks the current consumption at the normal operating frequency and at one other point every interval (every second or less). If a change is found at either of these two frequencies the controller will flag a possible change of state (i.e. the device may have changed from wet to dry or from dry to wet). This change will result in a call of the full scan.

In one embodiment, for the full scan the algorithm calculates a slope/differential of the drive current at each frequency step. As the algorithm steps through the frequencies, it measures the current and then subtracts the current measurement taken 16 frequency steps previously using a rolling shift register.

The invention is not limited to the embodiments described but may be varied in construction and detail.

The invention claimed is:

1. A nebulizer, comprising:
   a vibrating aperture plate mounted within the nebulizer and driven by an actuator; and
   an aperture plate drive circuit coupled to the actuator and having a controller, wherein the controller is configured to:
      measure an electrical drive parameter at each of a plurality of measuring points, each measuring point of the plurality of measuring points being associated with a drive frequency output by the drive circuit;
      perform a short scan at which the electrical drive parameter is measured at each of two or more measuring points associated with different drive frequencies; and
      according to drive parameter measurements at these two or more measuring points, determine if a full scan sweeping across a larger number of measuring points should be performed after completion of a predetermined time delay.

2. A nebulizer as claimed in claim 1, wherein the short scan has fewer than five measuring points.

3. A nebulizer as claimed in claim 1, wherein the controller is configured to compare measurements with tolerance ranges, and if a measurement falls outside its associated tolerance range, the full scan is initiated.

4. A nebulizer as claimed in claim 3, wherein the tolerance ranges are pre-defined.

5. A nebulizer as claimed in claim 1, wherein the short scan is performed at regular intervals.

6. A nebulizer as claimed in claim 5, wherein the intervals are sub-second.

7. A nebulizer as claimed in claim 1, wherein the full scan has five to three-hundred measuring points.

8. A nebulizer as claimed in claim 7, wherein the full scan has one-hundred to three-hundred measuring points.

9. A nebulizer as claimed in claim 1, wherein if it is determined that the full scan should be performed, performing the full scan after the predetermined time delay, and further wherein the controller is configured to dynamically determine, from the full scan, a frequency associated with at least one of the short scan measuring points.

10. A nebulizer as claimed in claim 9, wherein the controller is configured to select a frequency value corresponding to lowest drive current as a frequency for a short scan measuring point.

11. A nebulizer as claimed in claim 10, wherein said lowest drive current is determined to correspond to a resonant frequency, and a frequency value for the full scan measuring point with lowest drive current is stored for use as a short scan measuring point frequency.

12. A nebulizer as claimed in claim 1, wherein the electrical drive parameter is aperture plate drive current.

13. A nebulizer as claimed in claim 1, wherein the controller is configured to, during the full scan:
    dynamically perform a plurality of iterations, and
    in each iteration, compare the measured electrical drive parameter against a measurement at a previous measuring point to determine an end-of-dose indication and/or a selected drive frequency, wherein the end-of-dose indication is indicative of an end of an aerosolization cycle of the nebulizer, and wherein the selected drive frequency is a frequency between a resonant frequency and a non-resonant frequency.

14. A nebulizer as claimed in claim 13, wherein the controller is further configured to determine a slope value from the comparison and identify the end-of-dose when the slope value is above a threshold.

15. A nebulizer as claimed in claim 1, wherein the predetermined time delay is five seconds.

16. A method of operation of a nebulizer comprising a vibrating aperture plate mounted in the nebulizer and driven by an actuator, the actuator being coupled to an aperture plate drive circuit having a controller, wherein the method comprises:

measuring an electrical drive parameter at each of a plurality of measuring points, each measuring point being associated with a drive frequency output by the drive circuit; and performing a short scan at which a parameter is measured at each of two or more measuring points associated with different drive frequencies, and according to drive parameter measurements at the two or more measuring points, determining if a full scan sweeping across a larger number of measuring points should be performed after a predetermined time delay.

17. A method as claimed in claim 16, wherein the short scan has fewer than five measuring points and the full scan has five to three-hundred measuring points.

18. A method as claimed in claim 16, wherein the controller compares measurements with tolerance ranges, and if a measurement falls outside its associated range, a full scan is initiated.

19. A method as claimed in claim 16, wherein the short scan is performed at regular sub-second intervals.

20. A method as claimed in claim 16, wherein the predetermined time delay is five seconds.

* * * * *